(12) United States Patent
Moreno-Sevilla

(10) Patent No.: US 8,178,765 B2
(45) Date of Patent: May 15, 2012

(54) WHEAT CULTIVAR LA01425

(75) Inventor: Benjamin Moreno-Sevilla, Lafayette, IN (US)

(73) Assignee: Monsanto Technology LLC, St. Louis, MO (US)

( * ) Notice: Subject to any disclaimer, the term of this patent is extended or adjusted under 35 U.S.C. 154(b) by 337 days.

(21) Appl. No.: 12/484,920

(22) Filed: Jun. 15, 2009

(65) Prior Publication Data

US 2010/0319082 A1 Dec. 16, 2010

(51) Int. Cl.
*A01H 5/00* (2006.01)
*A01H 5/10* (2006.01)
*C12N 15/82* (2006.01)

(52) U.S. Cl. ............ 800/320.3; 800/260; 800/263; 800/264; 800/279; 800/281; 800/300; 800/301; 800/302; 800/303; 435/410

(58) Field of Classification Search ............ None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 7,053,286 B2 * | 5/2006 | Edge et al. | 800/320.3 |

OTHER PUBLICATIONS

Eshed, et al., 1996. Less-than-additive epistatic interactions of quantitative trait loci in tomato. Genetics 143:1807-1817.
Kraft, et al., 2000. Linkage disequilibrium and fingerprinting in sugar beet. Theor. Appl. Genet. 101:323-326.
US PVP Certificate No. 9200162, Pioneer Hi-Bred International, Inc., dated Apr. 30, 1993, 15 pages.

* cited by examiner

*Primary Examiner* — Cynthia Collins
(74) *Attorney, Agent, or Firm* — SNR Denton US LLP

(57) ABSTRACT

A wheat cultivar, designated LA01425, is disclosed. The invention relates to the seeds of wheat cultivar LA01425, to the plants of wheat LA01425, and to methods for producing a wheat plant produced by crossing wheat cultivar LA01425 with itself or another wheat variety. The invention also relates to methods for producing a wheat plant containing in its genetic material one or more transgenes and to the transgenic wheat plants and plant parts produced by those methods. The invention also relates to wheat varieties or breeding varieties and plant parts derived from wheat cultivar LA01425, to methods for producing other wheat varieties, lines or plant parts derived from wheat cultivar LA01425, and to the wheat plants, varieties, and their parts derived from the use of those methods. The invention further relates to hybrid wheat seeds and plants produced by crossing wheat cultivar LA01425 with another wheat cultivar.

23 Claims, No Drawings

WHEAT CULTIVAR LA01425

BACKGROUND OF THE INVENTION

The present invention relates to a wheat seed, a wheat plant, a wheat cultivar and a wheat hybrid. This invention further relates to a method for producing wheat seed and plants. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. In wheat, the important traits include increased yield and quality, resistance to diseases and insects, resistance to drought and heat, and improved agronomic traits.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to popular cultivars in environments representative of the commercial target area(s) for three or more years. The best lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefore, development of new cultivars is a time-consuming process that requires precise forward planning, efficient use of resources, and a minimum of changes in direction.

A most difficult task is the identification of individuals that are genetically superior because, for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The goal of a commercial wheat breeding program is to develop new, unique and superior wheat cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic and soil conditions, and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the same original parents and the same selection techniques. This unpredictability results in the expenditure of large amounts of research moneys to develop superior new wheat cultivars.

Pureline cultivars of wheat are commonly bred by hybridization of two or more parents followed by selection. The complexity of inheritance, the breeding objectives and the available resources influence the breeding method. Pedigree breeding, recurrent selection breeding and backcross breeding are breeding methods commonly used in self pollinated crops such as wheat. These methods refer to the manner in which breeding pools or populations are made in order to combine desirable traits from two or more cultivars or various broad-based sources. The procedures commonly used for selection of desirable individuals or populations of individuals are called mass selection, plant-to-row selection and single seed descent or modified single seed descent. One, or a combination of these selection methods, can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by selfing $F_1$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or, to further select individual plants. Once a progeny row or progeny hill is selected as having desirable traits it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

The single seed descent procedure in the strict sense refers to planting a segregating population, harvesting one seed from every plant, and combining these seeds into a bulk which is planted the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using off-season nurseries.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. However, SSR technology is currently the most efficient and practical marker technology; more marker loci can be routinely used and more alleles per marker locus can be found using SSRs in comparison to RFLPs. For example, see Song, Q. J. et al. "Development and mapping of microsatellite (SSR) markers in wheat" (*Theor. Appl. Genet.* 2005 110(3):550-560.) SNPs may also be used to identify the unique genetic composition of the invention and progeny varieties retaining that unique genetic composition. Various molecular marker techniques may be used in combination to enhance overall resolution.

Gel electrophoresis is particularly useful in wheat. Wheat variety identification is possible through electrophoresis of gliadin, glutenin, albumin, globulin, and total protein extracts (Bietz, J. A., pp. 216-228, "Genetic and Biochemical Studies of Nonenzymatic Endosperm Proteins" In *Wheat and Wheat Improvement*, ed. E. G. Heyne, 1987).

Molecular markers, which include markers identified through the use of techniques such as Starch Gel Electrophoresis, Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation breeding is another method of introducing new traits into wheat varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993.

The production of double haploids can also be used for the development of homozygous lines in the breeding program. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. Various methodologies of making double haploid plants in wheat have been developed (Laurie, D. A. et al., *Plant Breeding*, 1991, 106:182-189: Singh, N. et al., *Cereal Research Communications*, 2001, 29:289-296; Redha, A. et al., *Plant Cell Tissue and Organ Culture*, 2000, 63:167-172; U.S. Pat. No. 6,362,393).

Though pure-line varieties are the predominate form of wheat grown for commercial wheat production hybrid wheat is also used. Hybrid wheats are produced with the help of cytoplasmic male sterility, nuclear genetic male sterility, or chemicals. Various combinations of these three male sterility systems have been used in the production of hybrid wheat.

Descriptions of other breeding methods that are commonly used for different traits and crops can be found in one of several reference books (e.g., Allard, 1960; Simmonds, 1979; Sneep, et al. 1979; Fehr, 1993).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, and the grower, processor and consumer; for special advertising and marketing and commercial production practices, and new product utilization. The testing preceding the release of a new cultivar should take into consideration research and development costs as well as technical superiority of the final cultivar. For seed-propagated cultivars, it must be feasible to produce seed easily and economically.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

The present invention relates to a wheat seed, a wheat plant, a wheat cultivar, a wheat hybrid and a method for producing a wheat plant and a wheat hybrid.

The present invention further relates to a method of producing wheat seeds and plants by crossing a plant of the instant invention with another wheat plant.

This invention further relates to the seeds of wheat cultivar LA01425, to the plants of wheat cultivar LA01425 and to methods for producing a wheat plant produced by crossing the wheat LA01425 with itself or another wheat cultivar. Thus, any such methods using the wheat cultivar LA01425 are part of this invention, including selfing, backcrosses, hybrid production, crosses to populations, and the like.

In another aspect, the present invention provides for single trait converted plants of LA01425. The single transferred trait may preferably be a dominant or recessive allele. Preferably, the single transferred trait will confer such traits as herbicide resistance, insect resistance, resistance for bacterial, fungal, or viral disease, male fertility, male sterility, and industrial usage. The single trait may be a naturally occurring wheat gene or a transgene introduced through genetic engineering techniques.

In another aspect, the present invention provides regenerable cells for use in tissue culture of wheat plant LA01425. The tissue culture will preferably be capable of regenerating plants having the physiological and morphological characteristics of the foregoing wheat plant, and of regenerating plants having substantially the same genotype as the foregoing wheat plant. Preferably, the regenerable cells in such tissue cultures will be embryos, protoplasts, meristematic cells, callus, plant clumps, pollen, ovules, awn, pericarp, seeds, flowers, florets, heads, spikes, leaves, roots, root tips, anthers, stems, and the like. Still further, the present invention provides wheat plants regenerated from the tissue cultures of the invention.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. Allele is any of one or more alternative forms of a gene, all of which relate to one trait or characteristic. In a diploid cell or organism, the two alleles of a given gene occupy corresponding loci on a pair of homologous chromosomes.

Awn. Awn is intended to mean the elongated needle-like appendages on the flower- and seed-bearing "head" at the top of the cereal grain plant (e.g., wheat, common wheat, rye). Awns are attached to the lemmas. Lemmas enclose the stamen and the stigma as part of the florets. Florets are grouped in spikelets, which in turn together comprise the head.

Backcrossing. Backcrossing is a process in which a breeder repeatedly crosses hybrid progeny back to one of the parents, for example, a first generation hybrid $F_1$ with one of the parental genotypes of the $F_1$ hybrid.

Cell. Cell as used herein includes a plant cell, whether isolated in tissue culture or incorporated in a plant or plant part.

Disease Resistance. As used herein, the term "disease resistance" is defined as the ability of plants to restrict the activities of a specified pest, such as an insect, fungus, virus, or bacterium.

Disease Tolerance. As used herein, the term "disease tolerance" is defined as the ability of plants to endure a specified pest (such as an insect, fungus, virus or bacterium) or an adverse environmental condition and still perform and produce in spite of this disorder.

Embryo. The embryo is the small plant contained within a mature seed.

Essentially all of the physiological and morphological characteristics. A plant having essentially all of the physiological and morphological characteristics means a plant having the physiological and morphological characteristics of the recurrent parent, except for the characteristics derived from the converted trait.

Gene. As used herein, "gene" refers to a segment of nucleic acid. A gene can be introduced into a genome of a species, whether from a different species or from the same species, using transformation or various breeding methods.

Gene Converted (Conversion). Gene converted (conversion) plant refers to plants which are developed by backcrossing, genetic engineering or mutation wherein essentially all of the desired morphological and physiological characteristics of a variety are recovered in addition to the one or more traits transferred into the variety via the backcrossing technique, genetic engineering or mutation.

Gene Silencing. The interruption or suppression of the expression of a gene at the level of transcription or translation.

Genotype. Refers to the genetic constitution of a cell or organism.

Head. As used herein, the term "head" refers to a group of spikelets at the top of one plant stem. The term "spike" also refers to the head of a plant located at the top of one plant stem.

Kernel Weight. As used herein, the term "kernel weight" refers to the weight of individual kernels (also called seeds), often reported as the weight of one thousand kernels or "1000 Kernel Weight".

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging. As used herein, the term "lodging" refers to the bending or breakage of the plant stem, or the tilting over of the plant, which complicates harvest and can diminish the value of the harvested product.

Maturity. As used herein, the term "maturity" refers to the stage of plant growth at which the development of the kernels is complete.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two wheat varieties. Percent identity is determined by comparing a statistically significant number of the homozygous alleles of two developed varieties. For example, a percent identity of 90% between wheat variety 1 and wheat variety 2 means that the two varieties have the same allele at 90% of their loci.

Percent Similarity. Percent similarity as used herein refers to the comparison of the homozygous alleles of a wheat variety such as LA01425 with another plant, and if the homozygous allele of LA01425 matches at least one of the alleles from the other plant then they are scored as similar. Percent similarity is determined by comparing a statistically significant number of loci and recording the number of loci with similar alleles as a percentage. A percent similarity of 90% between LA01425 and another plant means that LA01425 matches at least one of the alleles of the other plant at 90% of the loci.

Plant. As used herein, the term "plant" includes reference to an immature or mature whole plant, including a plant from which seed or grain or anthers have been removed. A seed or embryo that will produce the plant is also considered to be the plant.

Plant Height (Hgt). As used herein, the term "plant height" is defined as the average height in inches or centimeters of a group of plants, as measured from the ground level to the tip of the head, excluding awns.

Plant Parts. As used herein, the term "plant parts" (or a wheat plant, or a part thereof) includes but is not limited to protoplasts, callus, leaves, stems, roots, root tips, anthers, pistils, seed, grain, pericarp, embryo, pollen, ovules, cotyledon, hypocotyl, spike, floret, awn, lemma, shoot, tissue, petiole, cells, meristematic cells and the like.

Progeny. As used herein, progeny includes an $F_1$ wheat plant produced from the cross of two wheat plants where at least one plant includes wheat cultivar LA01425. Progeny further includes but is not limited to subsequent $F_2$, $F_3$, $F_4$, $F_5$, $F_6$, $F_7$, $F_8$, $F_9$ and $F_{10}$ generational crosses with the recurrent parental line.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Septoria Leaf Blotch or Speckled Leaf Blotch. A disease of wheat, common wheat and durum wheat characterized by irregularly shaped blotches that are at first yellow and then turn reddish brown with grayish brown dry centers, caused by the rust fungus Septoria tritici.

Stripe Rust. A disease of wheat, common wheat, durum wheat, and barley characterized by elongated rows of yellow spores on the affected parts, caused by a rust fungus, Puccinia striformis. Resistance to this disease is scored on scales that reflect the observed extent of the disease on the leaves of the plant. In ratings on a scale of 1 to 5, 1 indicates resistant (no lesions or productions of spores) and 5 indicates highly susceptible (lesions covering all or most of the surface of the leaves). In ratings on a scale of 1 to 8, 1 indicates that lesions cover 0 to 3% of the second leaf from the top (the leaf below the top leaf) and 8 indicates that lesions cover 96 to 100%. Intervening ratings on the 1 to 8 scale indicate: 2=4 to 14%, 3=15 to 29%, 4=30 to 49%, 5=50-69%, 6=70 to 84%, 7=85 to 95% and 8=96 to 100%.

Test Weight (TWT). As used herein, the term "test weight" is a measure of density that refers to the weight in pounds of the amount of kernels contained in a bushel unit of volume.

DETAILED DESCRIPTION OF THE INVENTION

Wheat is grown worldwide and is the most widely adapted cereal. There are six main wheat market classes: Triticum aestivum L. classes (common wheat), hard red winter, hard red spring, soft red winter, and white; the sixth class is durum (Triticum turgidum L.). Common wheats are used in a variety of food products such as bread, cookies, cakes, crackers, and noodles. In general the hard wheat classes are milled into flour used for breads and the soft wheat classes are milled into flour used for pastries and crackers. Wheat starch is used in the food and paper industries, as laundry starches, and in other products. Because of its use in baking, the grain quality of wheat is very important. To test the grain quality of wheat for use as flour, milling properties are analyzed. Important milling properties are relative hardness or softness, weight per bushel of wheat (test weight), siftability of the flour, break flour yield, middlings flour yield, total flour yield, flour ash content, and wheat-to-flour protein conversion. Good processing quality for flour is also important. Good quality characteristics for flour from soft wheats include low to medium-low protein content, a low water absorption, production of large-diameter test cookies and large volume cakes. Wheat glutenins and gliadins, which together confer the properties of elasticity and extensibility, play an important role in the grain quality. Changes in quality and quantity of these proteins change the end product for which the wheat can be used.

Common wheat and wheat have many similarities in their pattern of plant development and morphology. The flower heads or spikes, develop at the top of the main stems and secondary stems called tillers, which are analogous to branches. An individual plant usually has a main stem and multiple tillers, the number of which depends on plant density, soil moisture, nutrient supply, pest damage, seeding date, and temperature, as well as the genetics of the plant. Typically, two to four tillers per plant will develop to the point of developing a head. Each head at the top of the stem consists of multiple spikelets, each of which consists of multiple florets that produce pollen, ovules, and ultimately, kernels.

Wheat has many benefits to offer crop producers, livestock feeders, and for commercial use in soft-dough mixtures. Its major strength is its versatility: it can be used for human consumption, grazing, silage, feed, cover crops and straw. Additionally, production of wheat provides environmental benefits such as erosion control and improved nutrient cycling through crop rotation. Thus, because of its considerable benefits, significant plant breeding effort has been directed towards breeding wheat.

Wheat is an important and valuable field crop. Thus, a continuing goal of wheat plant breeders is to develop stable, high yielding wheat cultivars that are agronomically sound. To accomplish this goal, the wheat breeder must select and develop plants that have the traits that result in superior cultivars.

The development of new wheat cultivars requires the evaluation and selection of parents and the crossing of these parents. The lack of predictable success of a given cross requires that a breeder, in any given year, make several crosses with the same or different breeding objectives.

The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

Wheat cultivar LA01425 is a soft-red, winter-type, common wheat bred for fall planting in the Midwest and Eastern United States. The primary usage of wheat cultivar LA01425 will be for production of grain, but it can also be used for production of silage harvested in the soft dough stage.

The variety has shown uniformity and stability, as described in the following variety description information in Table 1. It has been self-pollinated a sufficient number of generations with careful attention to uniformity of plant type. The line has been increased with continued observation for uniformity.

TABLE 1

VARIETY DESCRIPTION INFORMATION

Plant:

| | |
|---|---|
| Species: | *Triticum aestivum* |
| Kind: | Common |
| Vernalization: | Winter |
| Coleoptile anthocyanin: | Absent |
| Juvenile plant growth: | Erect |
| Plant color at boot stage: | Green |
| Flag leaf at boot stage: | Recurved, waxy bloom present |
| Heading: | 134 Julian days (equal to variety P25R47) |
| Anther color: | Yellow |
| Plant height (from soil to top of head, excluding awns): | 91 cm (5 cm more than variety P25R47) |

Stem:

| | |
|---|---|
| Anthocyanin: | Absent |
| Waxy bloom: | Present |

Internode:

| | |
|---|---|
| Form: | Hollow |
| Number: | 5 |
| Hairiness of last internode of rachis: | Absent |

Peduncle:

| | |
|---|---|
| Form: | Erect |
| Length: | 16 cm |

TABLE 1-continued

VARIETY DESCRIPTION INFORMATION

Auricle:

| | |
|---|---|
| Anthocyanin: | Absent |
| Hair: | Present |

Head (at maturity):

| | |
|---|---|
| Density: | Mid-dense |
| Shape: | Tapering |
| Curvature: | Inclined |
| Awnedness: | Awned |

Glumes (at maturity):

| | |
|---|---|
| Color: | Tan |
| Shoulder: | Wanting |
| Shoulder width: | Narrow |
| Beak: | Acuminate and narrow |
| Glume Length: | Long (0.9 cm) |
| Width: | Medium (0.35 cm) |
| Pubescence: | Absent |

Seed:

| | |
|---|---|
| Shape: | Ovate |
| Cheek: | Rounded |
| Brush: | Short |
| Brush collar: | Not collared |
| Crease width: | Narrow, less than 60% of kernel |
| Crease depth: | Mid-depth, less than 35% of kernel |
| Color: | Red |
| Texture: | Soft |
| Seed Weight: | 34 grams per 1000 kernels |
| Germ Size: | Small |
| Phenol reaction: | Black/brown |

Disease Reactions:

| | |
|---|---|
| *Puccinia graminis* f. sp. *tritici* (Stem rust): | Susceptible |
| *Puccinia striiformis* (Stripe rust): | Tolerant |
| *Septoria nodorum* (Glume blotch): | Intermediate |
| *Septoria tritici* (Speckled leaf blotch): | Tolerant |
| *Fusarium* spp (Scab): | Intermediate |
| *Puccinia recondita* f. sp. *tritici* (Leaf rust): | Tolerant |
| *Erysiphe graminis* f. sp. *tritici* (Powdery mildew): | Resistant |
| *Rhizoctonia solani* (*Rhizoctonia* root rot): | Intermediate |
| Soilborne mosaic virus (SBMV): | Intermediate |

Insect reactions:

| | |
|---|---|
| Hessian fly (*Mayetiola destructor*): | Susceptible |

This invention is also directed to methods for producing a wheat plant by crossing a first parent wheat plant with a second parent wheat plant, wherein the first or second wheat plant is the wheat plant from the cultivar LA01425. Further, both the first and second parent wheat plants may be the cultivar LA01425 (e.g., self-pollination). Further, the first or second parent may be a common wheat cultivar. Therefore, any methods using the cultivar LA01425 are part of this invention: selfing, backcrosses, hybrid breeding, and crosses to populations. Any plants produced using cultivar LA01425 as a parent are within the scope of this invention. As used herein, the term "plant" includes plant cells, plant protoplasts, plant cells of tissue culture from which wheat plants can be regenerated, plant calli, plant clumps, and plant cells that are intact in plants or parts of plants, such as pollen, flowers, embryos, ovules, seeds, pericarp, leaves, stems, roots, root tips, anthers, pistils, florets, awns, lemmas, heads, spikelets and the like. Thus, another aspect of this invention is to provide for cells which upon growth and differentiation produce a cultivar having essentially all of the physiological and morphological characteristics of LA01425.

The present invention contemplates a wheat plant regenerated from a tissue culture of a cultivar (e.g., LA01425) or hybrid plant of the present invention. As is well known in the art, tissue culture of wheat can be used for the in vitro regeneration of a wheat plant. Tissue culture of various tissues of plants and regeneration of plants therefrom is well known and widely published.

FURTHER EMBODIMENTS OF THE INVENTION

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are introduced into the genome using transformation or various breeding methods are referred to herein collectively as "transgenes". In some embodiments of the invention, a transgenic variant of LA01425 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed wheat variety LA01425.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

One embodiment of the invention is a process for producing wheat variety LA01425 further comprising a desired trait, said process comprising introducing a transgene that confers a desired trait to a wheat plant of variety LA01425. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including; a polynucleotide conferring resistance to imidazolinone, dicamba, sulfonylurea, glyphosate, glufosinate, triazine, benzonitrile, cyclohexanedione, phenoxy proprionic acid and L-phosphinothricin; a polynucleotide encoding a *Bacillus thuringiensis* polypeptide, a polynucleotide encoding phytase, FAD-2, FAD-3, galactinol synthase or a raffinose synthetic enzyme; or a polynucleotide conferring resistance to *Fusarium*, *Septoria*, or various viruses or bacteria.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (*Maydica* 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A genetic trait which has been engineered into the genome of a particular wheat plant may then be moved into the genome of another variety using traditional breeding techniques that are well known in the plant breeding arts. For example, a backcrossing approach is commonly used to move a transgene from a transformed wheat variety into an already developed wheat variety, and the resulting backcross conversion plant would then comprise the transgene(s).

Various genetic elements can be introduced into the plant genome using transformation. These elements include, but are not limited to genes, coding sequences, inducible, constitutive, and tissue specific promoters, enhancing sequences, and signal and targeting sequences. For example, see the traits, genes and transformation methods listed in U.S. Pat. No. 6,118,055.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed wheat plants, using transformation methods as described below to incorporate transgenes into the genetic material of the wheat plant(s).

Expression Vectors for Wheat Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Other selectable marker genes for plant transformation that are not of bacterial origin include, for example, mouse dihydrofolate reductase, plant 5-enolpyruvyl-shikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

In vivo methods for visualizing GUS activity that do not require destruction of plant tissue are available. Molecular Probes publication 2908, Imagene Green, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Expression Vectors for Wheat Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in wheat. Optionally, the inducible promoter is operably linked to a nucleotide sequence encoding a signal sequence which is operably linked to a gene for expression in wheat. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in wheat or the constitutive promoter is operably linked to a nucleotide sequence encoding a signal sequence which is operably linked to a gene for expression in wheat.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); PEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in wheat. Optionally, the tissue-specific promoter is operably linked to a nucleotide sequence encoding a signal sequence which is operably linked to a gene for expression in wheat. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a wheat plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered or mutated to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A gene conferring resistance to a pest, such as nematodes. See e.g., PCT Applications WO 96/30517, WO 93/1918, WO 03/033651 and Urwin et. al., *Planta* 204:472-479 (1998).

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyper-accumulation of a monoterpene, a sesquiterpene, a steroid, a hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. *Fusarium* head blight along with deoxynivalenol both produced by the pathogen *Fusarium graminearum* (Schwabe) have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome-inactivating proteins, flavonoids and lactoferricin. During infection with *Fusarium graminearum* deoxynivalenol is produced. There is evidence that production of deoxynivalenol increases the virulence of the disease. Genes with properties for detoxification of deoxynivalenol (Adam and Lemmens, In *International Congress on Molecular Plant-Microbe Interactions*, 1996; McCormick et al. *Appl. Environ. Micro.* 65:5252-5256 (1999)) have been engineered for use in wheat. A synthetic peptide that competes with deoxynivalenol has been identified (Yuan et al., *Appl. Environ. Micro.* 65:3279-3286 (1999)). Changing the ribosomes of the host so that they have reduced affinity for deoxynivalenol has also been used to reduce the virulence of *Fusarium graminearum*. Genes used to help reduce *Fusarium* head blight include but are not limited to Tri101 (*Fusarium*), PDR5 (yeast), tlp-1 (oat), tlp-2 (oat), leaf tlp-1 (wheat), tlp (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tlp (*Arabidopsis*), zeamatin (maize), type 1 RIP (barley), NPR1 (*Arabidopsis*), lactoferrin (mammal), oxalyl-CoA-decarboxylase (bacterium), IAP (baculovirus), ced-9 (*C. elegans*), and glucanase (rice and barley).

U. A gene, for example, the H9, H10 and H21 genes, conferring resistance to a pest, such as Hessian fly, stem soft fly, cereal leaf beetle, and/or green bug. See Liu, X. M. et al., *Theoretical and Applied Genetics*. 111:1308-1315 (2005).

V. A gene conferring resistance to diseases such as wheat rusts, *Septoria tritici*, *Septoria nodorum*, powdery mildew, *Helminthosporium* diseases, smuts, bunts, *Fusarium* diseases, bacterial diseases, and viral diseases. See for example, Cox, T. S., et al., *Crop Science*. 34(2):339-343 (1994), Raupp, W. J., et al., *Theoretical and Applied Genetics*. 102(2-3):347-352 (201), Brown-Guedina, G., "Tagging New Leaf Rust Resistance Genes in Wheat" in *Agricultural Research*. 49(5): 19 (May 2001), Chartrain, L., et al., *Plant Pathology*. 53:454-460 (2004), Shi, A. N., et al., *Phytopathology*. 88(2):144-147 (1998), Dahleen, L. S., et al., *Crop Science*. 41:628-637 (2001) and Mujeeb-Kazi, A., et al., "Transferring alien genes from related species and genera for wheat improvement" in *Bread Wheat Improvement and Production*, Eds. Curtis, B. C., et al. (2002).

W. Genes involved in the Systemic Acquired Resistance (SAR) Response and/or the pathogenesis-related genes.

Briggs, S., *Current Biology*, 5(2) (1995); Pieterse & Van Loon (2004) *Curr. Opin. Plant Bio.* 7(4):456-64 and Somssich (2003) *Cell* 113(7):815-6.

X. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2): 137-149 (1998). Also see U.S. Pat. No. 6,875,907.

Y. Detoxification genes, such as for fumonisin, beauvericin, moniliformin and zearalenone and their structurally related derivatives. For example, see U.S. Pat. No. 5,792,931.

Z. Cystatin and cysteine proteinase inhibitors. See U.S. Pat. No. 7,205,453.

AA. Defensin genes. See WO 03/000863 and U.S. Pat. No. 6,911,577.

BB. Genes conferring resistance to nematodes. See e.g. PCT Application WO 96/30517; PCT Application WO 93/19181, WO 03/033651, Urwin et al., *Planta* 204:472-479 (1998), and Williamson (1999) *Curr Opin Plant Bio.* 2(4): 327-31.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvylshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content. 1) Introduction of a phytase-encoding gene enhances breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., *Maydica* 35: 383 (1990) and/or by altering inositol kinase activity as in WO 02/059324, US2003/0009011, WO 03/027243, US2003/0079247, WO 99/05298, U.S. Pat. No. 6,197,561, U.S. Pat. No. 6,291,224, U.S. Pat. No. 6,391,348, WO 2002/059324, U.S. Pat. No. 2003/0079247, WO98/45448, WO99/55882, WO01/04147.

C. Modified carbohydrate composition effected, for example, by transforming plants with a gene coding for an enzyme that alters the branching pattern of starch, or, a gene altering thioredoxin such as NTR and/or TRX (See U.S. Pat. No. 6,531,648 which is incorporated by reference for this purpose) and/or a gamma zein knock out or mutant such as cs27 or TUSC27 or en27 (See U.S. Pat. No. 6,858,778 and US2005/0160488, US2005/0204418; which are incorporated by reference for this purpose). See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* alpha-amylase), Elliot et al., *Plant Molec. Biol.* 21: 515 (1993) (nucleotide sequences of tomato invertase genes), Sogaard et al., *J. Biol. Chem.* 268: 22480 (1993) (site-directed mutagenesis of barley alpha-amylase gene), and Fisher et al., *Plant Physiol.* 102: 1045 (1993) (maize endosperm starch branching enzyme II), WO 99/10498 (improved digestibility and/or starch extraction through modification of UDP-D-xylose 4-epimerase, Fragile 1 and 2, Ref 1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Elevated oleic acid via FAD-2 gene modification and/or decreased linolenic acid via FAD-3 gene modification. See U.S. Pat. Nos. 6,063,947; 6,323,392; and international publication WO 93/11245.

E. Altering conjugated linolenic or linoleic acid content, such as in WO 01/12800. Altering LEC1, AGP, Dek1, Superal1, mi1ps, various Ipa genes such as Ipa1, Ipa3, hpt or hggt. For example, see WO 02/42424, WO 98/22604, WO 03/011015, U.S. Pat. No. 6,423,886, U.S. Pat. Nos. 6,197, 561, 6,825,397, 7,157,621 and 7,425,442, WO 02/057439, WO 03/011015 and Rivera-Madrid, R. et al. *Proc. Natl. Acad. Sci.* 92:5620-5624 (1995).

F. Altered antioxidant content or composition, such as alteration of tocopherol or tocotrienols. For example, see U.S. Pat Nos. 6,787,683 and 7,154,029 and WO 00/68393 involving the manipulation of antioxidant levels through alteration of a phytl prenyl transferase (ppt), WO 03/082899 through alteration of a homogentisate geranyl geranyl transferase (hggt).

G. The content of high-molecular weight gluten subunits (HMS-GS). Genomic clones have been isolated for different subunits (Anderson et al., 1988, In *Proceedings of the 7th International Wheat Genetics Symposium*, IPR, pp. 699-704; Shewry et al. 1989, In *Oxford Surveys of Plant Molecular and Cell Biology*, pp. 163-219; Shewry et al. *Journal of Cereal Sci.* 15:105-120, 1992). Blechl et al. (*Journal of Plant Phys.* 152(6): 703-707, 1998) have transformed wheat with genes that encode a modified HMW-GS. See also U.S. Pat. Nos. 5,650,558; 5,914,450; 5,985,352; 6,174,725; and 6,252,134, which are incorporated herein by reference for this purpose.

H. Increased protein metabolism, zinc and iron content, for example, by regulating the NAC gene (See Uauy, C., et al., *Science*. 314:1298-1300 (2006), increased protein metabolism by regulating the Gpc-B1 gene (See Uauy, C., et al., *J. of Experimental Botany*. 57:2785-2794 (2006)) or Gpc-6B1 locus (See Distelfeld, A., et al., *Functional and Integrative Genomics*. 4:59-66 (2004) and Olmos, S. et al., *Theoretical and Applied Genetics*. 107:1243-1251 (2003) or regulating glutenin and gliadin genes (See Eagles, H. A., et al., *Australian J. of Agricultural Research*. 57(2):179 (2006) and Qi, P. F., et al., *Molecular Biology*. 40(5):713 (2006).

I. Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 98/56935 (plant amino acid biosynthetic enzymes), WO 98/45458 (engineered seed protein having higher percentage of essential amino acids), WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 96/01905 (increased threonine), WO 95/15392 (increased lysine), U.S. Pat. Nos. 6,930,225, 7,179,955, U.S. 2004/0068767, U.S. Pat. No. 6,803,498, WO 01/79516, and WO 00/09706 (Ces A: cellulose synthase), U.S. Pat. No. 6,194,638 (hemicellulose), U.S. Pat. No. 6,399,859 and U.S. Pat. No. 7,098,381 (UDPGdH), U.S. Pat. No. 6,194,638 (RGP).

4. Genes that Control Male Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

For additional examples of nuclear male and female sterility systems and genes, see also, U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265, 640; all of which are hereby incorporated by reference for this purpose.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, *The Maize Handbook* ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

A. Genes that affect abiotic stress resistance (including but not limited to flowering, seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929, 305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 20040098764 or US 20040078852.

B. Improved tolerance to water stress from drought or high salt water condition. The HVA1 protein belongs to the group 3 LEA proteins that include other members such as wheat pMA2005 (Curry, J., et al., *Plant Molecular Biology.* 16(6): 1073-1076 (June 1991) and Curry, J., et al., *Plant Molecular Biology.* 21:907-912 (1993)), cotton D-7 (Baker, J., et al., *Plant Molecular Biology.* 11:277-291 (1988)), carrot Dc3 (Seffens, W. S., et al., *Developmental Genetics.* 11:65-76 (1990)), and rape pLEA76 (Harada et al., 1989). These proteins are characterized by 11-mer tandem repeats of amino acid domains which may form a probable amphophilic alpha-helical structure that presents a hydrophilic surface with a hydrophobic stripe (Baker et al., 1988, supra; Dure, L., et al., *Plant Molecular Biology.* 12:475-486 (1989) and Dure, L., *Plant Journal.* 3:363-369 (1993)). The barley HVA1 gene and the wheat pMA2005 gene (Curry et al., 1991 and Curry et al., 1993, supra) are highly similar at both the nucleotide level and predicted amino acid level. These two monocot genes are closely related to the cotton D-7 gene (Baker et al., 1988, supra) and carrot Dc3 gene (Seffens et al., 1990, supra) with which they share a similar structural gene organization (Straub, R. E., et al., *Nature Genetics.* 8:291-296 (1994)). There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried, J. L., et al., *Plant Physiology.* 102(1):125-131 (May 1993)). Studies on several Indica varieties of rice showed that the levels of group 2 LEA proteins (also known as dehydrins) and group 3 LEA proteins in roots were significantly higher in salt-tolerant varieties compared with sensitive varieties (Moons, A., et al., *Plant Physiology.* 107:177-186 (1995)). The barley HVA1 gene was transformed into wheat. Transformed wheat plants showed increased tolerance to water stress, (Sivamani, E. et al. *Plant Science.* 155:1-9 (2001) and U.S. Pat. No. 5,981,842.)

C. Another example of improved water stress tolerance is through increased mannitol levels via the bacterial mannitol-1-phosphate dehydrogenase gene. To produce a plant with a genetic basis for coping with water deficit, Tarczynski et al. (*Proc. Natl. Acad. Sci. USA,* 89:2600 (1992); WO 92/19731, published Nov. 12, 1992; *Science,* 259, 508 (1993)) introduced the bacterial mannitol-1-phosphate dehydrogenase gene, mtlD, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level. See also U.S. Pat. No. 5,780,709 and international publication WO 92/19731.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FRI), WO 97/29123, U.S. Pat. No. 6,794,560, U.S. Pat. No. 6,307,126 (GAI), WO 99/09174 (D8 and Rht), and WO 2004/076638 and WO 2004/031349 (transcription factors).

Methods for Wheat Transformation

Numerous methods for plant transformation have been developed, including biological and physical plant transformation protocols. See, for example, Miki et al., "Procedures for Introducing Foreign DNA into Plants" in *Methods in Plant Molecular Biology and Biotechnology,* Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology,* Glick B. R. and Thompson, J. E. Eds. (CRC Press, Inc., Boca Raton, 1993) pages 89-119.

A. *Agrobacterium*-Mediated Transformation. One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer. Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., (1991) *Bio/Technology* 9:996. Alternatively, liposome and spheroplast fusion have been used to introduce expression vectors into plants. Deshayes et al., (1985) *EMBO J.,* 4:2731; Christou et al., (1987) *Proc Natl. Acad. Sci. U.S.A.* 84:3962. Direct uptake of DNA into protoplasts using $CaCl_2$ precipitation, polyvinyl alcohol or poly-L-ornithine has also been reported. Hain et al., (1985) *Mol. Gen. Genet.* 199:161 and Draper et al., (1982) *Plant Cell Physiol.* 23:451. Electroporation of protoplasts and whole cells and tissues has also been described. Donn et al., (1990) In: *Abstracts of VIIth International Congress on Plant Cell and Tissue Culture* IAPTC, A2-38, p 53; D'Halluin et al., (1992) *Plant Cell* 4:1495-1505 and Spencer et al., (1994) *Plant Mol. Biol.* 24:51-61.

Following transformation of wheat target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular wheat cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Song Q. J. et. al, "Development and mapping of microsatellite (SSR) markers in wheat" *Theor. Appl. Genet.* 110(3):55-560 (2005).

Particular markers used for these purposes are not limited to any particular set of markers, but are envisioned to include any type of marker and marker profile which provides a means of distinguishing varieties. One method of comparison is to use only homozygous loci for LA01425.

In addition to being used for identification of wheat variety LA01425 and plant parts and plant cells of variety LA01425, the genetic profile may be used to identify a wheat plant produced through the use of LA01425 or to verify a pedigree for progeny plants produced through the use of LA01425. The genetic marker profile is also useful in breeding and developing backcross conversions.

The present invention comprises a wheat plant characterized by molecular and physiological data obtained from the representative sample of said variety deposited with the American Type Culture Collection (ATCC). Further provided by the invention is a wheat plant formed by the combination of the disclosed wheat plant or plant cell with another wheat plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

The SSR profile of wheat plant LA01425 can be used to identify plants comprising LA01425 as a parent, since such plants will comprise the same homozygous alleles as LA01425. Because the wheat variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of LA01425 in their development, such as LA01425 comprising a backcross conversion, transgene, or genetic sterility factor, may be identified by having a molecular marker profile with a high percent identity to LA01425. Such a percent identity might be 95%, 96%, 97%, 98%, 99%, 99.5% or 99.9% identical to LA01425.

The SSR profile of LA01425 also can be used to identify essentially derived varieties and other progeny varieties developed from the use of LA01425, as well as cells and other plant parts thereof. Progeny plants and plant parts produced using LA01425 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from wheat variety, as measured by either percent identity or percent similarity. Such progeny may be further characterized as being within a pedigree distance of LA01425, such as within 1, 2, 3, 4 or 5 or fewer cross-pollinations to a wheat plant other than LA01425 or a plant that has LA01425 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Gene Conversion

When the term "wheat plant" is used in the context of the present invention, this also includes any gene conversions of that variety. The term "gene converted plant" as used herein refers to those wheat plants which are developed by backcrossing, genetic engineering or mutation wherein essentially all of the desired morphological and physiological characteristics of a variety are recovered in addition to the one or more genes transferred into the variety via the backcrossing technique, genetic engineering or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9 or more times to the recurrent parent. The parental wheat plant which contributes the gene for the desired characteristic is termed the "nonrecurrent" or "donor parent". This terminology refers to the fact that the nonrecurrent parent is used one time in the backcross protocol and therefore does not recur. The parental wheat plant to which the gene or genes from the nonrecurrent parent are transferred is known as the recurrent parent as it is used for several rounds in the backcrossing protocol (Poehlman & Sleper, 1994; Fehr, 1993). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a wheat plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference for this purpose.

Introduction of a New Trait or Locus into LA01425

Variety LA01425 represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of LA01425

A backcross conversion of LA01425 occurs when DNA sequences are introduced through backcrossing (Fehr, 1993), with LA01425 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: *Proceedings Symposium of the Analysis of Molecular Data*, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Fehr, 1993). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance and herbicide resistance. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into LA01425 is at least 1, 2, 3, 4, 5, 6, 7, 8, 9 or 10. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops, P.* 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in wheat variety LA01425 comprises crossing LA01425 plants grown from LA01425 seed with plants of another wheat variety that comprise the desired trait or locus, selecting $F_1$ progeny plants that comprise the desired trait or locus to produce selected $F_1$ progeny plants, crossing the selected progeny plants with the LA01425 plants to produce backcross progeny plants, selecting for backcross progeny plants that have the desired trait or locus and the morphological characteristics of wheat variety LA01425 to produce selected backcross progeny plants; and backcrossing to LA01425 three or more times in succession to produce selected fourth or higher backcross progeny plants that comprise said trait or locus. The modified LA01425 may be further characterized as having the physiological and morphological characteristics of wheat variety LA01425 listed in Table 1 as determined at the 5% significance level when grown in the same environmental conditions and/or may be characterized by percent similarity or identity to LA01425 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration, which may also affect a desired trait if a functional nucleic acid is inserted at the integration site.

In addition, the above process and other similar processes described herein may be used to produce first generation progeny wheat seed by adding a step at the end of the process that comprises crossing LA01425 with the introgressed trait or locus with a different wheat plant and harvesting the resultant first generation progeny wheat seed.

A further embodiment of the invention is a backcross conversion of wheat variety LA01425. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat" by K. A. Lucken (pp. 444-452 In *Wheat and Wheat Improvement*, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), powdery mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtlD). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Using LA01425 to Develop Other Wheat Varieties

Wheat varieties such as LA01425 are typically developed for use in seed and grain production. However, wheat varieties such as LA01425 also provide a source of breeding material that may be used to develop new wheat varieties. Plant breeding techniques known in the art and used in a wheat plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of wheat varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.

Additional Breeding Methods

This invention is directed to methods for producing a wheat plant by crossing a first parent wheat plant with a second parent wheat plant wherein either the first or second parent wheat plant is variety LA01425. The other parent may be any other wheat plant, such as a wheat plant that is part of a synthetic or natural population. Any such methods using wheat variety LA01425 are part of this invention: selfing, sibbing, backcrosses, mass selection, pedigree breeding, bulk selection, hybrid production, crosses to populations, and the like. These methods are well known in the art and some of the more commonly used breeding methods are described below.

Descriptions of breeding methods can be found in one of several reference books (e.g., Allard, *Principles of Plant Breeding*, 1960; Simmonds, *Principles of Crop Improvement*, 1979).

The following describes breeding methods that may be used with wheat cultivar LA01425 in the development of further wheat plants. One such embodiment is a method for developing a cultivar LA01425 progeny wheat plant in a wheat plant breeding program comprising: obtaining the wheat plant, or a part thereof, of cultivar LA01425 utilizing said plant or plant part as a source of breeding material and selecting a wheat cultivar LA01425 progeny plant with molecular markers in common with cultivar LA01425 and/or with morphological and/or physiological characteristics selected from the characteristics listed in Tables 1 or 2. Breeding steps that may be used in the wheat plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of wheat cultivar LA01425 progeny wheat plants, comprising crossing cultivar LA01425 with another wheat plant, thereby producing a population of wheat plants, which, on average, derive 50% of their alleles from wheat cultivar LA01425. A plant of this population may be selected and repeatedly selfed or sibbed with a wheat cultivar resulting from these successive filial generations. One embodiment of this invention is the wheat cultivar produced by this method and that has obtained at least 50% of its alleles from wheat cultivar LA01425.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the invention includes wheat cultivar LA01425 progeny wheat plants comprising a combination of at least two cultivar LA01425 traits selected from the group consisting of those listed in Tables 1 and 2 or the cultivar LA01425 combination of traits listed in the Summary of the Invention, so that said progeny wheat plant is not significantly different for said traits than wheat cultivar LA01425. Using techniques described herein, molecular markers may be used to identify said progeny plant as a wheat cultivar LA01425 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of wheat cultivar LA01425 may also be characterized through their filial relationship with wheat cultivar LA01425, as for example, being within a certain number of breeding crosses of wheat cultivar LA01425. A breeding cross is a cross made to introduce new genetics into the progeny, and is distinguished from a cross, such as a self or a sib cross, made to select among existing genetic alleles. The lower the number of breeding crosses in the pedigree, the closer the relationship between wheat cultivar LA01425 and its progeny. For example, progeny produced by the methods described herein may be within 1, 2, 3, 4 or 5 breeding crosses of wheat cultivar LA01425.

Pedigree Breeding

Pedigree breeding starts with the crossing of two genotypes, such as LA01425 and another wheat variety having one or more desirable characteristics that is lacking or which complements LA01425. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a wheat variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new wheat varieties.

Therefore, an embodiment of this invention is a method of making a backcross conversion of wheat variety LA01425, comprising the steps of crossing a plant of wheat variety LA01425 with a donor plant comprising a desired trait, selecting an $F_1$ progeny plant comprising the desired trait, and backcrossing the selected $F_1$ progeny plant to a plant of wheat variety LA01425. This method may further comprise the step of obtaining a molecular marker profile of wheat variety LA01425 and using the molecular marker profile to select for a progeny plant with the desired trait and the molecular marker profile of LA01425. In one embodiment the desired trait is a mutant gene or transgene present in the donor parent.

Recurrent Selection and Mass Selection

Recurrent selection is a method used in a plant breeding program to improve a population of plants. LA01425 is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into wheat variety LA01425. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, 1993, *Principles of Cultivar Development* Macmillan Publishing Company. In addition, mutations created in other wheat plants may be used to produce a backcross conversion of wheat cultivar LA01425 that comprises such mutation.

Further embodiments of the invention are the treatment of LA01425 with a mutagen and the plant produced by mutagenesis of LA01425. Information about mutagens and mutagenizing seeds or pollen are presented in the IAEA's *Manual on Mutation Breeding* (IAEA, 1977) other information about mutation breeding in wheat can be found in C. F. Konzak, 1987 "Mutations and Mutation Breeding" chapter 7B, of *Wheat and Wheat Improvement*, Second edition, Ed. Heyne.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing wheat cultivar LA01425.

Isozyme Electrophoresis and RFLPs have been widely used to determine genetic composition. See for example, S. J. O'Brien (ed.) *Genetic Maps: Locus Maps of Complex Genomes*. Cold Spring Harbor Laboratory Press. (1993) Cold Spring Harbor, N.Y.) and R. L. Phillips and I. K. Vasil (ed.) *DNA-based markers in plants*. 1994 Kluwer Academic Press Dordrecht, the Netherlands.

SSR technology is currently the most efficient and practical marker technology; more marker loci can be routinely used and more alleles per marker locus can be found using SSRs in comparison to RFLPs. Single Nucleotide Polymorphisms (SNPs) may also be used to identify the unique genetic composition of the invention and progeny varieties retaining that unique genetic composition. Various molecular marker techniques may be used in combination to enhance overall resolution.

Wheat DNA molecular marker linkage maps have been rapidly constructed and widely implemented in genetic studies. Sequences and PCR conditions of SSR Loci in wheat may be found in Kuleung, C. et al., (2006), "Evaluating the Genetic Diversity of Triticale with Wheat and Rye SSR Markers" *Crop Sci.* 46(4):1692-1700 and references cited therein and in Nicot, N. et al., (2004), "Study of simple sequence repeat (SSR) markers from wheat expressed sequence tags (ESTs)" *Theor. Appl. Genet.* 109(4):800-805.

One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a wheat plant for which wheat cultivar LA01425 is a parent can be used to produce double haploid plants. Double haploids are produced by the doubling of a set of chromosomes (1 N) from a heterozygous plant to produce a completely homozygous individual. For example, see Wan et al., 1989 "Efficient Production of Doubled Haploid Plants Through Colchicine Treatment of Anther-Derived Maize Callus", *Theor. Appl. Genet.*, 77:889-892 and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, *Am. Nat.* 93:381-382; Sharkar et al., 1966, *Genetics* 54:453-464), KEMS (Deimling et al., 1997, *Vortr. Pflanzenzuchtg* 38:203-224), or KMS and ZMS (Chalyk et al., 1994, *MNL* 68:47; Chalyk et al., 2000, *Plant Breeding* 119:363-364), and indeterminate gametophyte (ig) mutation (Kermicle 1969, *Science* 166:1422-1424). The disclosures of which are incorporated herein by reference for this purpose.

Methods for obtaining haploid plants are also disclosed in Kobayashi, M. et al., 1980, *J. Heredity* 71(1):9-14; Pollacsek, M., 1992, *Agronomie* (Paris) 12(3):247-251; Cho-Un-Haing et al., 1996, *J. Plant Biol.*, 39(3):185-188; Genetic Manipulation in Plant Breeding, Proceedings International Symposium Organized by EUCARPIA, Sep. 8-13, 1985, Berlin, Germany; Chalyk et al., 1994, *Maize Genet Coop*. Newsletter 68:47.

Thus, an embodiment of this invention is a process for making a substantially homozygous LA01425 progeny plant by producing or obtaining a seed from the cross of LA01425 and another wheat plant and applying double haploid methods to the $F_1$ seed or $F_1$ plant or to any successive filial generation. Based on studies in maize and currently being conducted in wheat, such methods would decrease the number of generations required to produce a variety with similar genetics or characteristics to LA01425. See Bernardo, R., et al., 2001, *Theor. Appl. Genet.* 102:986-992.

In particular, a process of making seed retaining the molecular marker profile of wheat variety LA01425 is contemplated, such process comprising obtaining or producing $F_1$ seed for which wheat variety LA01425 is a parent, inducing doubled haploids to create progeny without the occurrence of meiotic segregation, obtaining the molecular marker profile of wheat variety LA01425, and selecting progeny that retain the molecular marker profile of LA01425.

Descriptions of other breeding methods that are commonly used for different traits and crops can be found in one of several reference books (e.g., Allard, 1960; Simmonds, 1979; Sneep et al., 1979; Fehr, 1993).

Further reproduction of the variety can occur by tissue culture and regeneration. Tissue culture of various tissues of wheat and regeneration of plants therefrom is well known and widely published. A review of various wheat tissue culture protocols can be found in "In Vitro Culture of Wheat and Genetic Transformation-Retrospect and Prospect" by Maheshwari et al. (*Critical Reviews in Plant Sciences,* 14(2): pp 149-178, 1995). Thus, another aspect of this invention is to provide cells which upon growth and differentiation produce wheat plants having the physiological and morphological characteristics of wheat cultivar LA01425.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, ovules, pericarp, flowers, florets, heads, spikelets, seeds, leaves, stems, roots, root tips, anthers, pistils, awns, stems, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, describe certain techniques.

TABLES

As shown in Table 2, wheat cultivar LA01425 is compared to 31 different commercial wheat cultivars for yield in bushels per acre and for test weight in 2008 at 18 different locations in the eastern and mid-western United States. The various wheat cultivars were then ranked according to yield and test weight. In Table 2, column 1 shows the cultivar name or ID; for each location listed across the top of the table, the first column shows the yield, the second column shows the rank based on the yield and test weight for each cultivar at that location, and the third column shows the test weight. For some locations the test weight is not provided. At the bottom of the table, the mean, coefficient of variation (CV) and least significant difference (LSD) are given for each location.

TABLE 2

Comparison of Yield in Bushels per Acre and Test Weight Between
LA01425 and 31 Different Commercial Wheat Cultivars over 18 Different Locations

|  | RENWOOD, VA | | | MT HOLLY, VA | | | NEWPORT, AR | |
| --- | --- | --- | --- | --- | --- | --- | --- | --- |
| ID | YIELD | RANK | TWT | YIELD | RANK | TWT | YIELD | RANK |
| Z03-1281 | 104.20 | 23 | 61.53 | 121.64 | 3 | 59.40 | 74.97 | 21 |
| P25R47 | 108.28 | 20 | 63.33 | 116.64 | 5 | 59.18 | 85.00 | 2 |
| LA01425 | 115.92 | 10 | 63.43 | 116.34 | 6 | 60.59 | 79.44 | 7 |
| W1-714 | 127.66 | 1 | 62.23 | 109.24 | 15 | 59.19 | 78.84 | 10 |
| SR36-064J | 114.42 | 11 | 62.50 | 113.81 | 9 | 59.50 | 86.25 | 1 |
| Z03-0496 | 120.31 | 4 | 63.23 | 113.40 | 10 | 61.04 | 79.67 | 6 |
| W1-967 | 103.65 | 25 | 53.83 | 112.26 | 11 | 58.23 | 81.07 | 4 |
| LA02*459 | 113.23 | 12 | 61.33 | 94.91 | 27 | 56.76 | 76.33 | 18 |
| LA02*249 | 117.29 | 8 | 61.93 | 103.17 | 19 | 60.68 | 76.96 | 16 |
| BRANSON | 111.43 | 15 | 60.80 | 103.79 | 18 | 59.46 | 77.51 | 14 |
| W1-101 | 118.36 | 7 | 60.90 | 116.32 | 7 | 60.51 | 75.81 | 20 |
| W2-532 | 95.58 | 29 | 62.23 | 103.12 | 20 | 59.74 | 84.07 | 3 |
| Z03-3352 | 122.46 | 3 | 63.50 | 104.70 | 17 | 58.47 | 78.44 | 11 |
| P25R56 | 96.69 | 26 | 61.37 | 109.47 | 14 | 57.10 | 73.74 | 24 |
| W1-968 | 120.26 | 5 | 61.53 | 126.63 | 1 | 60.26 | 77.04 | 15 |
| 21525c1* | 112.64 | 13 | 61.97 | 100.60 | 23 | 58.99 | 69.63 | 29 |
| W2-912 | 125.94 | 2 | 61.13 | 86.93 | 32 | 60.20 | 74.07 | 23 |
| INW0731 | 89.11 | 32 | 62.10 | 87.14 | 31 | 58.72 | 79.29 | 9 |
| LA02-923 | 95.97 | 28 | 61.93 | 92.78 | 30 | 58.07 | 79.30 | 8 |
| BR-018 | 119.88 | 6 | 62.90 | 116.05 | 8 | 59.80 | 74.31 | 22 |
| GX02-140 | 103.77 | 24 | 63.03 | 104.91 | 16 | 60.49 | 75.82 | 19 |
| BESS | 110.79 | 16 | 59.90 | 98.59 | 25 | 60.80 | 71.99 | 26 |
| Z00-3538 | 110.75 | 17 | 61.33 | 94.40 | 28 | 57.14 | 78.37 | 12 |
| W1-016 | 93.65 | 30 | 61.77 | 109.66 | 13 | 60.52 | 76.64 | 17 |
| W2-960 | 112.25 | 14 | 63.20 | 93.65 | 29 | 57.41 | 66.69 | 31 |
| W2-053 | 104.42 | 22 | 61.60 | 123.29 | 2 | 61.10 | 81.02 | 5 |

TABLE 2-continued

Comparison of Yield in Bushels per Acre and Test Weight Between
LA01425 and 31 Different Commercial Wheat Cultivars over 18 Different Locations

| | | | | | | | | |
|---|---|---|---|---|---|---|---|---|
| W1-018 | 109.62 | 18 | 62.63 | 98.93 | 24 | 58.96 | 70.85 | 28 |
| X03-1157 | 116.48 | 9 | 63.20 | 101.57 | 21 | 59.42 | 73.43 | 25 |
| Z03-3070 | 109.23 | 19 | 57.97 | 95.82 | 26 | 59.05 | 59.46 | 32 |
| BW4523 | 93.12 | 31 | 62.17 | 118.27 | 4 | 59.31 | 68.67 | 30 |
| LA02*203 | 96.65 | 27 | 62.10 | 100.90 | 22 | 59.60 | 77.73 | 13 |
| X03-016 G | 104.92 | 21 | 62.53 | 110.93 | 12 | 59.86 | 70.89 | 27 |
| GRAND MEAN | 109.34 | | 61.72 | 106.25 | | 59.36 | 76.04 | |
| CV | 16.96 | | 5.25 | 6.75 | | 1.30 | 5.90 | |
| LSD | 25.29 | | 4.42 | 9.78 | | 1.05 | 6.11 | |

| | CHARLESTON MO | | | KANSAS CITY MO | | | MARSHALL MO | | |
|---|---|---|---|---|---|---|---|---|---|
| ID | YIELD | RANK | TWT | YIELD | RANK | TWT | YIELD | RANK | TWT |
| Z03-1281 | 94.53 | 6 | 61.85 | 75.98 | 1 | 70.31 | 6 | 58.91 | |
| P25R47 | 85.63 | 13 | 61.95 | 71.60 | 4 | 71.04 | 5 | 62.43 | |
| LA0425 | 94.61 | 5 | 61.98 | 72.46 | 3 | 64.31 | 17 | 59.94 | |
| W1-714 | 84.98 | 16 | 62.16 | 67.06 | 9 | 68.77 | 9 | 60.30 | |
| SR36-064J | 98.83 | 1 | 62.04 | 53.79 | 29 | 63.42 | 18 | 62.77 | |
| Z03-0496 | 89.63 | 9 | 61.78 | 73.58 | 2 | 68.82 | 8 | 59.84 | |
| W1-967 | 90.23 | 8 | 61.85 | 61.79 | 18 | 74.38 | 1 | 60.40 | |
| LA02*459 | 95.36 | 4 | 62.03 | 55.72 | 28 | 62.75 | 19 | 59.04 | |
| LA02*249 | 93.66 | 7 | 61.95 | 63.63 | 14 | 66.89 | 15 | 58.75 | |
| BRANSON | 82.82 | 19 | 61.67 | 65.45 | 12 | 60.78 | 25 | 57.39 | |
| W1-101 | 84.76 | 17 | 62.02 | 68.36 | 7 | 61.20 | 24 | 59.25 | |
| W2-532 | 82.74 | 20 | 62.06 | 68.69 | 6 | 59.16 | 28 | 58.64 | |
| Z03-3352 | 89.56 | 10 | 61.80 | 63.00 | 15 | 67.38 | 13 | 58.24 | |
| P25R56 | 78.07 | 27 | 62.03 | 58.79 | 24 | 67.50 | 12 | 60.32 | |
| W1-968 | 97.71 | 2 | 61.86 | 60.36 | 21 | 58.29 | 29 | 60.17 | |
| 21525c1* | 78.35 | 26 | 62.02 | 60.55 | 20 | 72.04 | 3 | 58.20 | |
| W2-912 | 85.92 | 12 | 61.85 | 66.86 | 11 | 60.34 | 26 | 58.48 | |
| INW0731 | 87.39 | 11 | 61.82 | 62.75 | 16 | 71.24 | 4 | 59.63 | |
| LA02-923 | 85.23 | 15 | 62.01 | 45.15 | 31 | 69.11 | 7 | 60.02 | |
| BR-018 | 82.52 | 21 | 61.79 | 67.30 | 8 | 59.85 | 27 | 58.22 | |
| GX02-140 | 85.49 | 14 | 61.67 | 61.37 | 19 | 67.69 | 11 | 58.88 | |
| BESS | 79.72 | 23 | 61.96 | 66.88 | 10 | 65.61 | 16 | 60.30 | |
| Z00-3538 | 73.26 | 31 | 61.93 | 59.60 | 23 | 67.93 | 10 | 59.30 | |
| W1-016 | 84.63 | 18 | 61.93 | 62.33 | 17 | 54.81 | 32 | 58.42 | |
| W2-960 | 78.46 | 25 | 62.23 | 58.71 | 25 | 61.66 | 23 | 59.22 | |
| W2-053 | 82.02 | 22 | 61.79 | 57.23 | 26 | 57.40 | 30 | 60.71 | |
| W1-018 | 77.48 | 28 | 61.83 | 60.10 | 22 | 56.62 | 31 | 57.85 | |
| X03-1157 | 79.49 | 24 | 61.94 | 69.33 | 5 | 61.84 | 22 | 58.20 | |
| Z03-3070 | 71.06 | 32 | 61.97 | 48.57 | 30 | 72.65 | 2 | 57.88 | |
| BW4523 | 95.64 | 3 | 61.90 | 56.11 | 27 | 62.71 | 20 | 53.16 | |
| LA02*203 | 77.19 | 29 | 61.94 | 64.94 | 13 | 67.03 | 14 | 59.03 | |
| X03-016 G | 75.65 | 30 | 61.96 | 42.77 | 32 | 62.11 | 21 | 58.56 | |
| GRAND MEAN | 85.08 | | 61.92 | 62.21 | | 64.86 | | 59.14 | |
| CV | 6.14 | | 0.13 | 7.33 | | 7.43 | | 4.22 | |
| LSD | 7.13 | | 0.11 | 4.82 | | 6.57 | | 3.41 | |

| | HOPKINSVILLE, KY | | | PRINCETON, IN | | | FLORA, IL | | |
|---|---|---|---|---|---|---|---|---|---|
| ID | YIELD | RANK | TWT | YIELD | RANK | TWT | YIELD | RANK | TWT |
| Z03-1281 | 90.87 | 15 | 61.99 | 101.70 | 3 | 55.75 | 86.70 | 1 | 54.28 |
| P25R47 | 90.02 | 17 | 60.61 | 104.53 | 1 | 55.70 | 67.11 | 28 | 54.77 |
| LA0425 | 90.09 | 16 | 60.26 | 88.31 | 28 | 58.83 | 73.13 | 19 | 55.60 |
| W1-714 | 94.16 | 11 | 61.80 | 96.98 | 12 | 55.90 | 79.83 | 8 | 54.29 |
| SR36-064J | 99.23 | 6 | 61.91 | 97.81 | 9 | 55.42 | 77.49 | 9 | 53.30 |
| Z03-0496 | 108.36 | 1 | 61.57 | 100.46 | 4 | 59.11 | 77.20 | 11 | 56.75 |
| W1-967 | 95.99 | 9 | 60.45 | 104.52 | 2 | 55.21 | 83.63 | 4 | 52.49 |
| LA02*459 | 103.71 | 3 | 61.15 | 99.48 | 8 | 53.99 | 67.57 | 27 | 54.23 |
| LA02*249 | 101.26 | 5 | 60.91 | 93.79 | 16 | 56.69 | 74.68 | 16 | 54.98 |
| BRANSON | 90.93 | 14 | 61.57 | 100.06 | 6 | 57.16 | 77.41 | 10 | 54.70 |
| W1-101 | 94.20 | 10 | 61.72 | 94.50 | 15 | 54.27 | 68.35 | 26 | 55.62 |
| W2-532 | 89.37 | 18 | 62.03 | 100.06 | 5 | 55.68 | 82.46 | 5 | 56.20 |
| Z03-3352 | 106.69 | 2 | 61.57 | 97.22 | 11 | 57.39 | 80.50 | 6 | 57.38 |
| P25R56 | 87.76 | 19 | 61.80 | 99.88 | 7 | 56.64 | 73.65 | 18 | 56.09 |
| W1-968 | 85.14 | 22 | 61.87 | 92.01 | 22 | 57.87 | 59.22 | 31 | 55.60 |
| 21525c1* | 74.77 | 29 | 59.69 | 89.94 | 27 | 53.52 | 64.68 | 30 | 52.86 |
| W2-912 | 96.03 | 8 | 61.49 | 97.30 | 10 | 58.30 | 84.44 | 3 | 57.10 |
| INW0731 | 98.26 | 7 | 61.72 | 94.70 | 14 | 55.98 | 80.27 | 7 | 56.18 |
| LA02-923 | 103.11 | 4 | 61.76 | 96.90 | 13 | 56.61 | 76.42 | 12 | 53.87 |

TABLE 2-continued

Comparison of Yield in Bushels per Acre and Test Weight Between
LA01425 and 31 Different Commercial Wheat Cultivars over 18 Different Locations

| | | | | | | | | | |
|---|---|---|---|---|---|---|---|---|---|
| BR-018 | 74.43 | 30 | 61.68 | 93.18 | 20 | 56.40 | 73.89 | 17 | 56.44 |
| GX02-140 | 79.87 | 26 | 61.30 | 93.43 | 19 | 56.64 | 85.24 | 2 | 56.31 |
| BESS | 78.22 | 27 | 61.60 | 90.74 | 26 | 58.73 | 74.77 | 15 | 58.87 |
| Z00-3538 | 83.19 | 24 | 59.76 | 91.16 | 25 | 49.67 | 68.75 | 25 | 54.58 |
| W1-016 | 92.22 | 13 | 61.68 | 92.65 | 21 | 54.52 | 72.06 | 20 | 57.58 |
| W2-960 | 93.06 | 12 | 61.56 | 91.79 | 23 | 54.94 | 71.07 | 24 | 56.18 |
| W2-053 | 85.49 | 21 | 61.49 | 93.71 | 17 | 58.42 | 59.05 | 32 | 56.32 |
| W1-018 | 77.00 | 28 | 61.83 | 86.86 | 29 | 56.88 | 76.08 | 13 | 55.31 |
| X03-1157 | 84.23 | 23 | 62.03 | 91.66 | 24 | 57.45 | 75.67 | 14 | 55.04 |
| Z03-3070 | 85.75 | 20 | 56.16 | 84.09 | 32 | 50.33 | 71.62 | 22 | 53.53 |
| BW4523 | 73.86 | 31 | 61.22 | 93.51 | 18 | 57.44 | 71.17 | 23 | 56.82 |
| LA02*203 | 72.37 | 32 | 61.22 | 86.01 | 30 | 56.46 | 66.25 | 29 | 55.91 |
| X03-016 G | 82.57 | 25 | 61.60 | 85.54 | 31 | 53.75 | 71.70 | 21 | 52.80 |
| GRAND MEAN | 89.44 | | 61.22 | 94.52 | | 55.99 | 74.13 | | 55.37 |
| CV | 8.38 | | 0.81 | 3.37 | | 1.69 | 8.78 | | 1.92 |
| LSD | 10.22 | | 0.68 | 4.35 | | 1.29 | 8.87 | | 1.45 |

| | LAFAYETTE, IN | | | ATLANTA, IN | | | WABASH, IN | | |
|---|---|---|---|---|---|---|---|---|---|
| ID | YIELD | RANK | TWT | YIELD | RANK | TWT | YIELD | RANK | TWT |
| Z03-1281 | 93.88 | 1 | 57.73 | 106.12 | 4 | 60.61 | 90.21 | 16 | 56.29 |
| P25R47 | 81.01 | 14 | 58.04 | 107.58 | 2 | 60.16 | 95.13 | 2 | 57.60 |
| LA0425 | 85.37 | 6 | 59.31 | 97.95 | 12 | 60.45 | 90.43 | 11 | 58.65 |
| W1-714 | 78.10 | 24 | 58.45 | 105.13 | 5 | 61.12 | 90.36 | 14 | 56.76 |
| SR36-064J | 86.31 | 3 | 56.26 | 93.02 | 20 | 61.52 | 92.72 | 8 | 54.94 |
| Z03-0496 | 80.68 | 15 | 56.79 | 98.22 | 10 | 61.65 | 89.47 | 20 | 55.53 |
| W1-967 | 83.17 | 12 | 56.62 | 86.35 | 29 | 60.56 | 93.50 | 6 | 54.41 |
| LA02*459 | 88.02 | 2 | 55.71 | 113.27 | 1 | 60.67 | 94.91 | 3 | 55.23 |
| LA02*249 | 73.61 | 30 | 58.93 | 89.24 | 23 | 59.47 | 88.56 | 24 | 57.19 |
| BRANSON | 74.86 | 28 | 57.34 | 100.03 | 7 | 60.41 | 91.05 | 10 | 57.15 |
| W1-101 | 84.14 | 11 | 58.93 | 94.36 | 19 | 60.68 | 90.37 | 13 | 54.89 |
| W2-532 | 84.43 | 9 | 58.37 | 89.05 | 24 | 61.46 | 90.29 | 15 | 56.31 |
| Z03-3352 | 78.53 | 21 | 58.39 | 94.70 | 16 | 61.11 | 90.39 | 12 | 55.95 |
| P25R56 | 79.11 | 19 | 57.83 | 100.81 | 6 | 60.80 | 98.68 | 1 | 55.75 |
| W1-968 | 75.18 | 27 | 59.88 | 97.26 | 13 | 61.07 | 89.14 | 23 | 58.09 |
| 21525c1* | 84.22 | 10 | 58.25 | 106.85 | 3 | 60.87 | 94.55 | 4 | 55.99 |
| W2-912 | 72.98 | 31 | 59.08 | 98.08 | 11 | 60.60 | 85.26 | 30 | 57.88 |
| INW0731 | 78.17 | 22 | 57.89 | 95.92 | 15 | 60.79 | 85.63 | 29 | 55.32 |
| LA02-923 | 85.85 | 4 | 56.68 | 89.01 | 25 | 60.30 | 94.55 | 5 | 55.66 |
| BR-018 | 84.95 | 7 | 59.09 | 92.87 | 21 | 60.45 | 89.76 | 18 | 57.39 |
| GX02-140 | 74.10 | 29 | 58.51 | 87.27 | 28 | 60.58 | 89.43 | 21 | 56.37 |
| BESS | 80.26 | 17 | 59.13 | 99.67 | 8 | 61.00 | 83.97 | 31 | 58.14 |
| Z00-3538 | 85.48 | 5 | 58.08 | 94.56 | 18 | 60.32 | 88.18 | 25 | 55.98 |
| W1-016 | 82.53 | 13 | 58.20 | 94.63 | 17 | 60.32 | 90.01 | 17 | 56.75 |
| W2-960 | 78.15 | 23 | 57.72 | 86.15 | 30 | 60.79 | 91.11 | 9 | 56.23 |
| W2-053 | 78.05 | 25 | 60.38 | 83.69 | 31 | 60.32 | 85.87 | 27 | 59.04 |
| W1-018 | 79.09 | 20 | 58.91 | 96.90 | 14 | 60.74 | 89.58 | 19 | 57.21 |
| X03-1157 | 76.65 | 26 | 58.15 | 87.56 | 27 | 61.24 | 85.94 | 26 | 54.81 |
| Z03-3070 | 84.93 | 8 | 58.17 | 98.66 | 9 | 60.50 | 93.29 | 7 | 56.65 |
| BW4523 | 65.64 | 32 | 60.29 | 91.54 | 22 | 61.03 | 80.65 | 32 | 58.58 |
| LA02*203 | 79.82 | 18 | 59.90 | 88.58 | 26 | 60.89 | 85.69 | 28 | 58.80 |
| X03-016 G | 80.60 | 16 | 57.64 | 82.62 | 32 | 59.73 | 89.41 | 22 | 55.75 |
| GRAND MEAN | 80.56 | | 58.27 | 95.24 | | 60.69 | 89.94 | | 56.60 |
| CV | 4.29 | | 0.92 | 7.20 | | 0.62 | 3.07 | | 0.89 |
| LSD | 4.72 | | 0.73 | 9.35 | | 0.52 | 3.76 | | 0.69 |

| | WOODBURN, IN | | | COVINGTON, OH | | | CELINA, OH | | |
|---|---|---|---|---|---|---|---|---|---|
| ID | YIELD | RANK | TWT | YIELD | RANK | TWT | YIELD | RANK | TWT |
| Z03-1281 | 86.27 | 14 | 55.37 | 91.03 | 2 | 52.28 | 105.44 | 10 | 61.09 |
| P25R47 | 91.97 | 4 | 56.55 | 91.95 | 1 | 52.53 | 109.35 | 2 | 60.93 |
| LA0425 | 97.49 | 1 | 57.49 | 88.10 | 5 | 53.10 | 107.93 | 4 | 61.37 |
| W1-714 | 92.17 | 3 | 55.61 | 87.50 | 8 | 52.41 | 107.28 | 5 | 61.84 |
| SR36-064J | 85.28 | 17 | 53.09 | 87.75 | 7 | 52.17 | 104.68 | 13 | 62.12 |
| Z03-0496 | 86.60 | 12 | 55.83 | 87.84 | 6 | 52.75 | 101.14 | 21 | 62.56 |
| W1-967 | 89.23 | 9 | 52.34 | 88.43 | 3 | 51.02 | 107.14 | 6 | 61.04 |
| LA02*459 | 85.18 | 18 | 53.42 | 88.11 | 4 | 51.62 | 105.46 | 9 | 61.19 |
| LA02*249 | 91.04 | 6 | 55.60 | 87.23 | 9 | 52.36 | 108.45 | 3 | 61.23 |
| BRANSON | 92.24 | 2 | 55.99 | 86.97 | 11 | 52.16 | 119.68 | 1 | 61.91 |
| W1-101 | 84.91 | 20 | 54.19 | 85.34 | 15 | 52.02 | 99.94 | 23 | 61.42 |
| W2-532 | 90.78 | 7 | 55.74 | 85.48 | 14 | 52.54 | 105.68 | 8 | 61.59 |
| Z03-3352 | 86.10 | 15 | 54.65 | 85.50 | 13 | 52.50 | 98.05 | 26 | 61.81 |
| P25R56 | 91.60 | 5 | 53.41 | 87.19 | 10 | 52.09 | 103.40 | 15 | 61.77 |

TABLE 2-continued

Comparison of Yield in Bushels per Acre and Test Weight Between
LA01425 and 31 Different Commercial Wheat Cultivars over 18 Different Locations

| | | | | | | | | |
|---|---|---|---|---|---|---|---|---|
| W1-968 | 84.84 | 21 | 56.09 | 84.40 | 17 | 52.74 | 98.95 | 25 | 61.33 |
| 21525c1* | 82.24 | 26 | 52.90 | 84.03 | 21 | 51.72 | 106.29 | 7 | 61.44 |
| W2-912 | 84.25 | 23 | 56.62 | 83.70 | 23 | 52.74 | 105.17 | 11 | 61.65 |
| INW0731 | 86.03 | 16 | 54.62 | 85.97 | 12 | 52.03 | 102.95 | 17 | 61.72 |
| LA02-923 | 85.05 | 19 | 53.68 | 84.51 | 16 | 51.99 | 99.35 | 24 | 60.94 |
| BR-018 | 89.38 | 8 | 55.38 | 82.91 | 25 | 52.47 | 95.39 | 29 | 61.74 |
| GX02-140 | 88.41 | 10 | 56.52 | 84.32 | 19 | 52.47 | 102.25 | 19 | 61.22 |
| BESS | 81.93 | 28 | 56.09 | 84.15 | 20 | 52.86 | 95.29 | 30 | 61.53 |
| Z00-3538 | 82.95 | 25 | 52.48 | 84.38 | 18 | 51.37 | 100.20 | 22 | 61.09 |
| W1-016 | 84.50 | 22 | 53.41 | 83.96 | 22 | 52.12 | 94.84 | 32 | 60.63 |
| W2-960 | 86.66 | 11 | 53.98 | 82.47 | 26 | 52.14 | 103.01 | 16 | 61.55 |
| W2-053 | 82.17 | 27 | 57.38 | 81.04 | 29 | 52.99 | 96.45 | 28 | 60.92 |
| W1-018 | 83.45 | 24 | 55.90 | 82.37 | 27 | 52.45 | 104.49 | 14 | 61.29 |
| X03-1157 | 86.42 | 13 | 54.72 | 83.10 | 24 | 52.21 | 95.12 | 31 | 61.69 |
| Z03-3070 | 80.02 | 30 | 55.53 | 80.66 | 30 | 51.22 | 105.04 | 12 | 61.75 |
| BW4523 | 76.70 | 32 | 56.65 | 79.03 | 32 | 52.52 | 96.91 | 27 | 61.39 |
| LA02*203 | 78.71 | 31 | 58.47 | 81.86 | 28 | 52.77 | 102.41 | 18 | 61.31 |
| X03-016 G | 80.93 | 29 | 56.11 | 80.51 | 31 | 51.96 | 101.30 | 20 | 60.93 |
| GRAND MEAN | 86.11 | | 55.18 | 85.06 | | 52.26 | 102.78 | | 61.44 |
| CV | 5.11 | | 1.55 | 9.34 | | 2.25 | 4.78 | | 0.77 |
| LSD | 6.00 | | 1.17 | 1.86 | | 0.30 | 6.70 | | 0.64 |

| | TIFFIN, OH | | | ARCHBOLD, OH | | | BLISFIELD, MI | | |
|---|---|---|---|---|---|---|---|---|---|
| ID | YIELD | RANK | TWT | YIELD | RANK | TWT | YLD | RANK | TWT |
| Z03-1281 | 108.84 | 14 | 59.68 | 81.11 | 10 | 60.79 | 78.74 | 14 | 61.76 |
| P25R47 | 111.76 | 6 | 59.80 | 88.66 | 3 | 58.91 | 80.52 | 6 | 60.18 |
| LA0425 | 116.54 | 1 | 60.15 | 90.08 | 2 | 60.79 | 81.44 | 5 | 62.07 |
| W1-714 | 110.15 | 11 | 60.13 | 86.22 | 5 | 58.28 | 82.42 | 4 | 58.19 |
| SR36-064J | 110.54 | 9 | 60.45 | 83.45 | 7 | 58.28 | 80.22 | 7 | 57.71 |
| Z03-0496 | 101.29 | 30 | 60.42 | 75.26 | 17 | 58.28 | 73.70 | 25 | 57.77 |
| W1-967 | 114.02 | 4 | 59.67 | 73.97 | 20 | 59.53 | 78.79 | 13 | 57.71 |
| LA02*459 | 110.84 | 8 | 60.02 | 77.11 | 16 | 58.28 | 75.41 | 21 | 60.00 |
| LA02*249 | 111.61 | 7 | 59.72 | 85.60 | 6 | 60.79 | 79.18 | 10 | 60.12 |
| BRANSON | 115.48 | 3 | 59.60 | 83.23 | 8 | 60.79 | 66.21 | 31 | 58.75 |
| W1-101 | 106.85 | 21 | 59.69 | 86.25 | 4 | 58.28 | 83.03 | 2 | 57.40 |
| W2-532 | 115.79 | 2 | 59.46 | 74.58 | 19 | 58.28 | 83.20 | 1 | 60.49 |
| Z03-3352 | 103.16 | 28 | 59.71 | 64.94 | 29 | 58.91 | 70.37 | 27 | 59.61 |
| P25R56 | 109.62 | 12 | 59.90 | 78.03 | 13 | 59.53 | 79.96 | 8 | 57.89 |
| W1-968 | 103.61 | 27 | 59.79 | 73.27 | 21 | 58.28 | 82.71 | 3 | 58.50 |
| 21525c1* | 110.43 | 10 | 59.75 | 96.49 | 1 | 60.79 | 71.80 | 26 | 60.10 |
| W2-912 | 107.96 | 18 | 59.64 | 68.61 | 26 | 62.04 | 67.14 | 30 | 59.80 |
| INW0731 | 108.19 | 17 | 59.66 | 77.53 | 15 | 59.53 | 75.76 | 18 | 55.65 |
| LA02-923 | 105.25 | 23 | 59.63 | 77.96 | 14 | 58.91 | 78.81 | 12 | 59.93 |
| BR-018 | 108.50 | 16 | 59.45 | 56.36 | 32 | 58.28 | 78.92 | 11 | 58.64 |
| GX02-140 | 113.29 | 5 | 59.78 | 61.56 | 30 | 60.79 | 75.25 | 22 | 58.16 |
| BESS | 105.73 | 22 | 60.18 | 75.23 | 18 | 60.79 | 76.86 | 17 | 57.71 |
| Z00-3538 | 109.05 | 13 | 59.79 | 80.06 | 12 | 60.16 | 65.61 | 32 | 58.96 |
| W1-016 | 106.90 | 20 | 59.41 | 65.17 | 28 | 59.53 | 74.75 | 23 | 57.71 |
| W2-960 | 100.43 | 31 | 59.73 | 80.70 | 11 | 58.91 | 77.25 | 15 | 58.44 |
| W2-053 | 104.37 | 25 | 59.58 | 81.80 | 9 | 60.16 | 75.55 | 20 | 59.85 |
| W1-018 | 108.67 | 15 | 59.69 | 69.86 | 25 | 60.79 | 75.59 | 19 | 59.77 |
| X03-1157 | 96.46 | 32 | 59.50 | 65.29 | 27 | 60.79 | 68.64 | 29 | 57.39 |
| Z03-3070 | 104.99 | 24 | 59.57 | 59.25 | 31 | 58.91 | 76.88 | 16 | 59.64 |
| BW4523 | 104.15 | 26 | 59.78 | 72.16 | 23 | 61.41 | 79.82 | 9 | 59.98 |
| LA02*203 | 102.04 | 29 | 59.59 | 72.54 | 22 | 62.04 | 73.86 | 24 | 60.04 |
| X03-016 G | 107.91 | 19 | 59.33 | 72.02 | 24 | 58.20 | 69.33 | 28 | 60.28 |
| GRAND MEAN | 107.95 | | 59.76 | 76.07 | | 59.67 | 76.18 | | 59.07 |
| CV | 2.95 | | 0.37 | 15.09 | | 1.60 | 11.29 | | 1.20 |
| LSD | 4.34 | | 0.30 | 15.66 | | 1.30 | 11.76 | | 0.97 |

| | 2008 AVE OVER 18 DIFFERENT LOC | | |
|---|---|---|---|
| ID | YIELD | RANK | TWT |
| Z03-1281 | 92.36 | 1 | 58.71 |
| P25R47 | 92.10 | 2 | 58.92 |
| LA0425 | 91.66 | 3 | 59.63 |
| W1-714 | 91.49 | 4 | 58.67 |
| SR36-064J | 90.50 | 5 | 58.37 |
| Z03-0496 | 90.31 | 6 | 59.06 |
| W1-967 | 90.12 | 7 | 57.21 |
| LA02*459 | 89.30 | 8 | 57.79 |

TABLE 2-continued

Comparison of Yield in Bushels per Acre and Test Weight Between
LA01425 and 31 Different Commercial Wheat Cultivars over 18 Different Locations

| | | | |
|---|---|---|---|
| LA02*249 | 89.21 | 9 | 58.83 |
| BRANSON | 88.89 | 10 | 58.55 |
| W1-101 | 88.73 | 11 | 58.24 |
| W2-532 | 88.03 | 12 | 58.80 |
| Z03-3352 | 87.87 | 13 | 58.81 |
| P25R56 | 87.44 | 14 | 58.40 |
| W1-968 | 87.00 | 15 | 59.06 |
| 21525c1* | 86.67 | 16 | 58.03 |
| W2-912 | 86.17 | 17 | 59.29 |
| INW0731 | 85.91 | 18 | 58.34 |
| LA02-923 | 85.80 | 19 | 58.25 |
| BR-018 | 85.58 | 20 | 58.76 |
| GX02-140 | 85.19 | 21 | 58.92 |
| BESS | 84.47 | 22 | 59.35 |
| Z00-3538 | 84.33 | 23 | 57.62 |
| W1-016 | 84.22 | 24 | 58.41 |
| W2-960 | 84.07 | 25 | 58.39 |
| W2-053 | 84.03 | 26 | 59.50 |
| W1-018 | 83.53 | 27 | 58.88 |
| X03-1157 | 83.27 | 28 | 58.61 |
| Z03-3070 | 82.33 | 29 | 57.43 |
| BW4523 | 82.20 | 30 | 58.98 |
| LA02*203 | 81.92 | 31 | 59.38 |
| X03-016 G | 81.76 | 32 | 58.19 |
| GR MEAN | 86.76 | | |
| CV | | | |
| LSD | | | |

As shown in Table 2, the wheat cultivar of the present invention, LA01425, performed well over the 18 different locations and ranked third over the 31 comparison wheat cultivars.

DEPOSIT INFORMATION

A deposit of the Monsanto Technology LLC proprietary Wheat Cultivar LA01425 disclosed above and recited in the appended claims has been made with the American Type Culture Collection (ATCC), 10801 University Boulevard, Manassas, Va. 20110. The date of deposit was Jul. 14, 2011. The deposit of 2,500 seeds was taken from the same deposit maintained by Monsanto Technology LLC since prior to the filing date of this application. All restrictions will be removed upon granting of a patent, and the deposit is intended to meet all of the requirements of 37 C.F.R. §§1.801-1.809. The ATCC Accession Number is PTA-11995. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter are interpreted to include all such modifications, permutations, additions, and sub-combinations as are within their true spirit and scope.

What is claimed is:

1. A seed of wheat cultivar LA01425, representative sample seed of said cultivar is deposited under ATCC Accession No. PTA-11995.

2. A wheat plant, or a part thereof, produced by growing the seed of claim 1.

3. A tissue culture produced from protoplasts or cells from the plant of claim 2, wherein said cells or protoplasts are produced from a plant part selected from the group consisting of head, awn, leaf, pollen, ovule, embryo, cotyledon, hypocotyl, meristematic cell, root, root tip, pistil, anther, floret, seed, pericarp, spike, stem, and callus.

4. A wheat plant regenerated from the tissue culture of claim 3.

5. A method for producing a wheat seed, said method comprising crossing two wheat plants and harvesting the resultant wheat seed, wherein at least one wheat plant is the wheat plant of claim 2.

6. A wheat seed produced by the method of claim 5.

7. A wheat plant, or a part thereof, produced by growing said seed of claim 6.

8. The method of claim 5, wherein at least one of said wheat plants is transgenic.

9. A method of producing an herbicide resistant wheat plant, wherein said method comprises introducing a gene conferring herbicide resistance into the plant of claim 2.

10. An herbicide resistant wheat plant produced by the method of claim 9, wherein the gene confers resistance to a herbicide selected from the group consisting of glyphosate, sulfonylurea, imidazolinone, dicamba, glufosinate; phenoxy proprionic acid, L-phosphinothricin, cyclohexone, cyclohexanedione, triazine, and benzonitrile.

11. A method of producing a pest or insect resistant wheat plant, wherein said method comprises introducing a gene conferring pest or insect resistance into the wheat plant of claim 2.

12. A pest or insect resistant wheat plant produced by the method of claim 11.

13. The wheat plant of claim 12, wherein the gene encodes a *Bacillus thuringiensis* (Bt) endotoxin.

14. A method of producing a disease resistant wheat plant, wherein said method comprises introducing a gene into the wheat plant of claim 2.

15. A disease resistant wheat plant produced by the method of claim 14.

16. A method of producing a wheat plant with modified fatty acid metabolism, modified carbohydrate metabolism or modified protein metabolism, wherein the method comprises introducing a gene encoding a protein selected from the group consisting of glutenins, gliadins, phytase, fructosyltransferase, levansucrase, α-amylase, invertase and starch branching enzyme or encoding an antisense of stearyl-ACP desaturase into the wheat plant of claim 2.

17. A wheat plant having modified fatty acid metabolism or modified carbohydrate metabolism produced by the method of claim 16.

18. A method of introducing a desired trait into wheat cultivar LA01425, wherein the method comprises:
(a) crossing a LA01425 plant, wherein a representative sample of seed is deposited under ATCC Accession No. PTA-11995, with a plant of another wheat cultivar that comprises a desired trait to produce progeny plants wherein the desired trait is selected from the group consisting of male sterility, herbicide resistance, insect resistance, modified fatty acid metabolism, modified carbohydrate metabolism, modified protein metabolism, modified phytic acid metabolism, modified waxy starch content, modified protein content, increased tolerance to water stress and resistance to bacterial disease, fungal disease or viral disease;
(b) selecting one or more progeny plants that have the desired trait to produce selected progeny plants;
(c) crossing the selected progeny plants with the LA01425 plant to produce backcross progeny plants;
(d) selecting for backcross progeny plants that have the desired trait and all of the physiological and morphological characteristics of wheat cultivar LA01425 listed in Table 1; and
(e) repeating steps (c) and (d) two or more times in succession to produce selected third or higher backcross progeny plants that comprise the desired trait and all of the physiological and morphological characteristics of wheat cultivar LA01425 listed in Table 1.

19. A wheat plant produced by the method of claim 18, wherein the plant has the desired trait.

20. The wheat plant of claim 19, wherein the desired trait is herbicide resistance and the resistance is conferred to an herbicide selected from the group consisting of imidazolinone, dicamba, cyclohexanedione, sulfonylurea, glyphosate, glufosinate, phenoxy proprionic acid, L-phosphinothricin, triazine and benzonitrile.

21. The wheat plant of claim 19, wherein the desired trait is insect resistance and the insect resistance is conferred by a gene encoding a *Bacillus thuringiensis* endotoxin.

22. The wheat plant of claim 19, wherein the desired trait is modified fatty acid metabolism, modified carbohydrate metabolism or modified protein metabolism, and said desired trait is conferred by a gene encoding a protein selected from the group consisting of glutenins, gliadins, phytase, fructosyltransferase, levansucrase, α-amylase, invertase and starch branching enzyme or DNA encoding an antisense of stearyl-ACP desaturase.

23. The wheat plant of claim 19, wherein the desired trait is male sterility and the trait is conferred by a gene that confers male sterility.

\* \* \* \* \*